# (12) United States Patent
Bevinakatti et al.

(10) Patent No.: US 8,603,959 B2
(45) Date of Patent: Dec. 10, 2013

(54) SURFACTANT COMPOUNDS

(75) Inventors: Hanamanthsa S Bevinakatti, Ingleby Barwick (GB); Alan G Waite, Darlington (GB)

(73) Assignee: Croda International PLC, Goole, North Humberside (GB)

( * ) Notice: Subject to any disclaimer, the term of this patent is extended or adjusted under 35 U.S.C. 154(b) by 1103 days.

(21) Appl. No.: 11/665,695

(22) PCT Filed: Oct. 18, 2005

(86) PCT No.: PCT/GB2005/004014
§ 371 (c)(1),
(2), (4) Date: Feb. 19, 2009

(87) PCT Pub. No.: WO2006/043048
PCT Pub. Date: Apr. 27, 2006

(65) Prior Publication Data
US 2009/0215629 A1    Aug. 27, 2009

(30) Foreign Application Priority Data
Oct. 18, 2004 (GB) .................................. 0423072.8

(51) Int. Cl.
*C11D 9/00* (2006.01)

(52) U.S. Cl.
USPC ........... 510/353; 510/158; 510/159; 510/276; 510/337; 510/389; 554/108; 554/169; 554/172; 514/785; 424/59; 507/138

(58) Field of Classification Search
None
See application file for complete search history.

(56) References Cited

U.S. PATENT DOCUMENTS

| | | | |
|---|---|---|---|
| 3,370,958 A | | 2/1968 | Freund et al. |
| 3,637,357 A | * | 1/1972 | Nixon et al. ................... 44/301 |
| 4,229,480 A | | 10/1980 | Suggs et al. |
| 4,383,937 A | * | 5/1983 | Williams ................. 252/389.62 |
| 5,513,712 A | * | 5/1996 | Sydansk ........................ 175/69 |
| 5,872,149 A | * | 2/1999 | Dralle-Voss et al. ......... 514/533 |
| 6,103,000 A | | 8/2000 | Custer |
| 6,340,244 B1 | * | 1/2002 | Fujita et al. ................... 384/462 |

FOREIGN PATENT DOCUMENTS

| | | | |
|---|---|---|---|
| EP | 0233684 | * | 8/1987 |
| EP | 0 752 468 A2 | | 1/1997 |
| EP | 1671617 | | 6/2006 |
| EP | 1614411 B1 | | 10/2011 |
| GB | 815179 | | 6/1959 |
| JP | 53-81796 | | 7/1978 |
| JP | 56012340 | * | 2/1981 |
| JP | 57 188487 A | | 11/1982 |
| JP | 61 056061 A | | 3/1986 |
| JP | 06 329166 A | | 11/1994 |
| JP | 09 104613 A | | 4/1997 |
| JP | 09104613 | * | 4/1997 |
| JP | 10-25224 | | 1/1998 |
| JP | 11-209231 | | 8/1999 |
| JP | 2005-112823 | | 4/2005 |
| WO | WO 2004/082645 | | 9/2004 |

OTHER PUBLICATIONS

JP 56012340, Novel Esterified Product and cosmetic and External Preparation containing the same, 1981, English Abstract, (1 page).*
JP 0910463, Water-in-oil Type Gelatinous Emusion composition and Emulsion Cosmetic or External Preparation using the same, 1997, English translation (27 pages).*
Feuge, R.O., et al., Polymeric Fats from Stearic, Oleic and Short-chain Dibasic acids, 1959, Industrial and Engineering Chemistry, vol. 51, No. 9, pp. 1019-1022.*
International Search Report for PCT/GB2005/004014 dated Dec. 6, 2005.
Office Action mailed Feb. 22, 2013 in corresponding Canadian Patent Application No. 2,582,598.
Office Action mailed Jul. 20, 2012 in corresponding Indian Patent Application No. 2751/DELNP/2007.
Wang, Yadong et al., "A Tough Biodegradable Elastomer," *Nature Biotechnology*, vol. 20 (2002) 602-606.
Office Action (English translation) mailed Jan. 10, 2012 in corresponding Japanese Patent Application No. 2007-536267.

* cited by examiner

*Primary Examiner* — Yate K Cutliff
(74) *Attorney, Agent, or Firm* — Jones Day

(57) ABSTRACT

Fatty esters of oligoesters of a dicarboxylic acid and a polyol retaining at least one free hydroxyl group, particularly of the formula (I): $R^1—[OR^2O—C(O)—R^3—(O)C—]_m—R^4$ (I), where $R^1$ is H, a monocarboxylic acid group, or $R^6O—[C(O)—R^3—(O)C]—$; $R^2$s are residues of polyols having at least one substituent free hydroxyl; $R^3$s are hydrocarbylene; $R^4$ is —OH, —OM where M is a salt forming metal, amine or ammonium, —$OR^6$, or —$OR^2O—R^7$; $R^5$ is $C_7$ to $C_{21}$ hydrocarbyl; $R^6$ is $C_8$ to $C_{22}$ hydrocarbyl; $R^7$ is H, or —$C(O)R^5$; and m is 1 to 20; provided that at least one of $R^1$ and $R^4$ is or includes a $C_8$ to $C_{22}$ group, are surfactants. A range of surfactant properties can be obtained by varying the molecules within these ranges. Especially where $R^2$ is derived from a higher polyol e.g. sorbitol, $R^3$ is $C_2$ to $C_6$, and the fatty terminal group is $C_8$ to $C_{14}$, the products can be highly water soluble and effective oil in water emulsifiers.

22 Claims, No Drawings

SURFACTANT COMPOUNDS

CROSS REFERENCE TO RELATED APPLICATION

This application is the National Phase application of International Application No. PCT/GB2005/004014, filed 18 Oct. 2005, which designates the United States and was published in English. This application, in its entirety, is incorporated herein by reference.

This invention relates to surfactant compounds which include oligo- or poly-meric esters made up of polyhydroxy hydrocarbyl, particularly saccharide, residues, and dicarboxylic acid residues, modified by the inclusion of a hydrophobic residue, and to the use of such compounds as surfactants, particularly as emulsifiers, especially in personal care formulations.

For effective surfactancy in water based systems, e.g. oil in water emulsions, or dispersing solids in water, it is usually desirable to use surfactants which are relatively hydrophilic, and are typically moderately water soluble. Such surfactants usually have a high HLB (Hydrophile/Lipophile Balance), typically greater than 7 and commonly in the range 8 to 18. Conventionally this has been achieved by using alcohol ethoxylates having relatively long polyoxyethylene chains, typically including at least 10 and sometimes up to about 100 EO groups, for alcohols having $C_{12}$ to $C_{18}$ chains, or by using fatty acid esters, usually mainly mono-esters of sugars such as sucrose.

Correspondingly for effective surfactancy in oil based systems it is desirable to use surfactants that are relatively hydrophobic, usually oil soluble and often water insoluble, typically having a low HLB e.g. less than 7 and commonly in the range 4 to 6.

The present invention is based on our finding that certain polyesters of polyols and dicarboxylic acids give intermediate oligomers or polymers that can be further esterified typically with monocarboxylic acids or monohydric alcohols to give compounds which have surfactant activity for example as oil in water emulsifiers. For convenience the intermediate materials may be simply referred to as oligoesters or oligomers.

The present invention accordingly provides a surfactant compound which is a fatty mono- or di-ester of a oligoester of a dicarboxylic acid and a polyol which after polyesterification retains at least one free hydroxyl group.

The compounds of the invention can be fatty acid mono- or di-esters of bis-hydroxyl ended oligoesters; fatty alcohol mono- or diesters of bis-carboxyl ended oligoesters; fatty acid or fatty alcohol mono-esters, or mixed fatty acid fatty alcohol bis-esters of mono-hydroxyl mono-carboxyl ended oligoesters and the invention includes these sub-types of compound.

In particular, the compounds of the invention are of the formula (I)

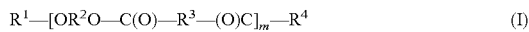

where
$R^1$ is H, a group $R^5(O)C—$, or a group $R^6O—[C(O)—R^3—O)C]—$;
each $R^2$ is independently a $C_3$ to $C_{10}$ hydrocarbyl group including at least 1 substituent free hydroxyl group;
each $R^3$ is independently a $C_1$ to $C_{20}$, particularly a $C_2$ to $C_{20}$, hydrocarbylene group;
$R^4$ is —OH, —OM where M is a salt forming metal, an amine or ammonium group, a group —$OR^6$, or a group —$OR^2O—R^7$;
$R^5$ is a $C_7$ to $C_{21}$ aliphatic hydrocarbyl group;
each $R^6$ is independently a $C_8$ to $C_{22}$ aliphatic hydrocarbyl group;
$R^7$ is H or a group —$C(O)R^5$ where $R^5$ is independently as defined above; and
m is from 1 to 20, particularly from 3 to 10, more particularly from 3.5 to 8;
provided that at least one of $R^1$ and $R^4$ is or includes a group including a $C_7$ to $C_{21}$ hydrocarbyl group.

Within the general formula (I) there are three main groups of compounds:
a) fatty acid mono- and bis-esters of bis-hydroxyl ended oligoester intermediates, having the formula (Ia):

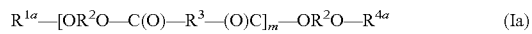

where
each $R^2$, each $R^3$ and m are independently as defined in formula (I);
$R^{1a}$ is a group $R^5(O)C—$; and
$R^{4a}$ is —H, or a group —$C(O)R^5$;
where each $R^5$ is independently as defined in formula (I);
b) fatty acid or fatty alcohol mono- and fatty acid fatty alcohol bis-esters of hydroxyl carboxyl ended oligoester intermediates, having the formula (Ib):

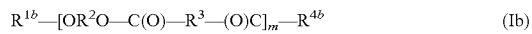

each $R^2$, each $R^3$ and m are independently as defined in formula (I);
$R^{1b}$ is H or a group $R^5(O)C—$;
$R^{4b}$ is —OH, —OM, where M is a salt forming metal {atom} or {an} amine or ammonium group, or a group —$OR^6$;
where each $R^5$ and $R^6$ is independently as defined in formula (I), provided that at least one of $R^{1b}$ and $R^{4b}$ is or includes a $C_8$ to $C_{22}$ group; and
c) fatty alcohol mono- and bis-esters of bis-carboxyl ended oligoester intermediates, having the formula (Ic):

each $R^2$, each $R^3$ and m are independently as defined in formula (I);
$R^{1c}$ is a group $R^6O—C(O)—R^3—(O)C—$; and
$R^{4c}$ is H or a salt forming metal {atom} or {an} amine or ammonium group or a group —$OR^6$;
where each $R^6$ is independently as defined in formula (I).

The compounds of the formula (Ia) include an "extra" residue of the polyol residue —$OR^2O—$ and as the residue —$OR^2O—$ are the main source of hydrophilicity in the molecule it is likely that such compounds will be intended to be relatively hydrophilic, commonly water soluble and particularly having an HLB value of from 8 to 18. It is likely that such compounds will use relatively short fatty monocarboxylic acid chains e.g. $C_8$ to $C_{14}$ particularly $C_{10}$ to $C_{12}$ in the final esters and will usually be mono-esters (di-esters being less hydrophilic).

Compounds of the formula (Ib) have equal numbers of polyol and dicarboxylic acid residues and are likely to be intermediate in their hydrophilicity and hydrophobicity depending on the particular residues used and the length of the fatty chain(s) in the final esters.

The compounds of the formula (Ic) include an "extra" residue of the —$C(O)—R^3—(O)C—$ dicarboxylic acid residue and as this is a source of hydrophobicity in the molecule it is likely that such compounds will be intended to be relatively hydrophobic, commonly water Insoluble, often oil soluble and particularly having an HLB value of from 4 to 6 and may have relatively longer fatty chains in the final ester e.g. derived from $C_{12}$ to $C_{20}$, particularly $C_{16}$ to $C_{18}$ alcohols.

Compounds of the formula (I) are linear compounds in that the oligoester chain is shown as not being branched or crosslinked and the fatty group in $R^1$ or $R^4$ is shown as terminal on the oligoester chain. As is discussed below, the polyols [typically of the formula (II): $HOR^2$—OH] used in making the compounds of the formula (I) have hydroxyl functionality >2, e.g. sorbitol has a total of 6 hydroxyl groups, so there is a possibility that branching reactions may take place, similarly the dicarboxylic acid [typically of the formula (III): HOOC—$R^3$—COOH] may include functionality that may enable branching e.g. further carboxyl group(s) or hydroxyl group(s). The compounds of the formula (I) have use as surfactants and in such uses it is desirable to avoid this type of branching as we believe it reduces the effectiveness of the compounds as surfactants. Desirably the proportion of such materials having a structure analogous to formula (I) but including branching in the oligoester chain is less than 20 wt %, more desirably less than 10 wt %, and particularly less than 5 wt % of the surfactant product.

The hydrocarbyl group $R^2$ can be considered as the residue of a corresponding polyol HO—$R^2$—OH (II) after removing two hydroxyl groups. $R^2$ is desirably an aliphatic hydrocarbyl group, which will usually be saturated, having from 3 to 10 and particularly 4 to 8, and especially 6, carbon atoms and it will usually be linear though it may include branching. The residue $R^2$ includes at least 1 and more usually from 1 to 6, particularly 1 to 4 and especially 4, hydroxyl groups which will usually be secondary hydroxyl groups (see also below).

To aid manufacture of the desired linear oligomeric intermediate products the polyol (II) desirably includes two relatively reactive hydroxyl groups, the remaining groups being substantially less reactive. Thus, in synthesis involving reaction of the polyol (II) with dicarboxylic acid (III) or a reactive derivative (see below), the predominant reaction is between the carboxylic acid groups and the more reactive hydroxyl groups to give linear oligomers [which are subsequently reacted with the monocarboxylic acid (IV) or a reactive derivative or alcohol (V) (see below)]. In particular, the polyol (II) will have two primary hydroxyl groups and 1 to 6, particularly 1 to 4 and especially 4, secondary hydroxyl groups.

Particularly desirably, $R^2$ is of the formula: —$(CH2)_{p1}(CHOH)_{p2}(CH2)_{p3}$— where p1 and p3 are each independently from 1 to 3, desirably 1, and p2 is from 1 to 6, more usually from 1 to 4. The corresponding polyols include glycerol, $C_4$ polyols such as threitol and erythritol, $C_5$ polyols such as inositol, arabitol and xylitol and $C_6$ polyols such as sorbitol. The $C_4$ to $C_6$ polyols are commonly the reduced or hydrogenated forms of the corresponding tetrose, pentose and hexose sugars. In such polyols there are two primary hydroxyl groups and 1 to 4 secondary hydroxyl groups. Usually it will be desirable to have a relatively large number of free hydroxyl groups to maximise the hydrophilic contribution of this part of the molecule, however, if desired the number of free hydroxyl groups can be less than the maximum possible e.g. 4 with sorbitol, either by reacting the groups e.g. by etherification or esterification, or by using modified polyols e.g. by forming sorbitan by the anhydridisation of sorbitol.

It is possible to include relatively small proportions of polyol residues which have no free hydroxyl groups e.g. as derived from ethylene, dlethylene, triethylene or propylene glycols or by reacting the polyol so that it only has 2 hydroxyl groups e.g. as in iso-sorbide derived by di-anhydridisation of sorbitol. However, as it is generally desirable to use this part of the molecule to provide hydrophilicity, the proportion of such residues will generally be low, typically an average of not more than 25 mol %, more usually not more than 10 mol %, and desirably not more than 5 mol % of the polyol residues in the molecule.

The group $R^3$ can be considered as the residue of the corresponding dicarboxylic acid HOOC—$R^3$—COOH (III) after removing the carboxylic acid groups and the dicarboxylic acid (III) or a reactive derivative will usually be the synthetic precursor providing the group $R^3$ to the compound of the invention. $R^3$ can be saturated or unsaturated, linear or branched and can be aromatic e.g. a phenyl ring (thus giving a phthalic, terephthalic or iso-phthalic dicarboxylic acid) or and desirably aliphatic, typically an alkylene or alkenylene group, and may be linear or branched, and may be cyclic though it is desirably open chain. Commonly $R^3$ is a group: —$(CH_2)_n$—, where n is from 1 to 10, usually from 2 to 10, particularly from 2 to 8, more particularly from 2 to 6. Because mixtures of different dicarboxylic acids (or reactive derivatives) may be used to make materials used in practice, n may appear to be non integral, because it will be an average. The group $R^3$ is usually unsubstituted, but may be substituted e.g. with further hydroxyl or carboxyl groups as in citric acid (which has both).

The $C_7$ to $C_{21}$ aliphatic hydrocarbyl group $R^5$ can be considered as the residue of the corresponding carboxylic, particularly fatty, acid: $R^5COOH$ (IV) and within the compounds of the invention usually appears as part of a carboxyl residue $R^5(O)C$—. Desirably, $R^5$ is a $C_7$ to $C_{17}$, alkyl, alkenyl or alkadienyl group. Generally within this range, it will be a $C_7$ to $C_{13}$ particularly a $C_9$ to $C_{13}$ group when the end product is desired to be hydrophilic and a $C_{15}$ to $C_{17}$ group when the end product is desired to be hydrophobic.

The group $R^6$ is a $C_8$ to $C_{22}$ hydrocarbyl group and can be considered as the residue of the corresponding, particularly fatty, alcohol $R^1OH$ (V) and within the compounds of the invention usually appears as part of a hydrocarbyloxy group —$OR^6$. Desirably, $R^6$ is a $C_8$ to $C_{18}$, group especially an alkyl, alkenyl or alkadienyl group.

Each group $R^5$ or $R^6$ is independently desirably an alkyl, alkenyl or alkadienyl group. In use it may be desired to use a mixture of compounds having different groups $R^5$ or $R^6$ respectively, e.g. as derived from naturally occurring fats and oils or as iso-stearic acid or iso-stearyl alcohol respectively. Further $R^5$ and $R^6$ may each independently be straight chain or branched e.g. as derived from iso-stearic acid or iso-stearyl alcohol respectively, and saturated as derived from lauric, palmitic, stearic or iso-stearic acids or lauryl, palmityl, stearyl or iso-stearyl alcohol respectively; or unsaturated as derived from oleic, linoleic or palmitoleic acids or oleyl, linoleyl or palmitoleyl alcohols respectively.

So-called "iso-stearic acid" is a commercially available material, e.g. from Uniqema, and is a mixture of acids having from 14 to 22, with about ⅔ having 18, carbon atoms, including short, mainly methyl but also including some ethyl, side chains, branching from the main chain mainly in the middle of the chain, typically about the 9-position e.g. from about the 6-position to about the 12-position, in an 18 carbon molecule. The assay molecular weight (e.g. by acid number) is close to that of stearic acid. "Iso-stearic acid" is a co-product (after separation and hydrogenation) from the manufacture of so-called "dimer acids" from $C_{18}$ unsaturated (mainly oleic and linoleic) fatty acids by catalytic thermal polymerisation.

M is a salt forming metal, an amine or ammonium group. Where M is metal it is particularly an alkali metal e.g. sodium or potassium atom; where M is amine it is particularly mono-, di- or tri-, alkyl or hydroxyalkyl amine, typically containing in total from 1 to 12 carbon atoms; and where M is ammonium, it may be unsubstituted or substituted e.g. with 1 to 4 alkyl groups, the typically containing in total from 1 to 16 carbon atoms.

The index m represents the average number of repeat units in oligomeric ester part of the molecule. Typically m will be at least 3, more usually at least 3.5, and desirably at least 5, though not usually more than 20 and desirably not more than 10 and will desirably be from 3.5, especially 4, to 7. As the number is an average, m may be non-integral.

The properties of the compounds of the invention, particularly the HLB can be varied by choice of the hydrophilic and hydrophobic components of the molecules. Thus increasing the length of the hydrocarbylene group $R^3$ and/or the groups $R^5$, and/or $R^6$, when these are hydrocarbyl, will give a more hydrophobic product; and increasing the number of free hydroxyl groups in the group $R^2$, generally linked with increasing length of the $R^2$ chain, will increase the hydrophilicity of the compounds of the formula (I). Further, the bis-hydroxyl ended oligoester intermediates will generally give more hydrophilic products that corresponding mono- or bis-carboxyl ended intermediates because they will have a (slightly) higher proportion of hydroxyl containing groups. Where the compounds of the formula (I) have a free carboxyl group, then they may have anionic surfactant properties as well as non-ionic properties, especially under alkaline conditions (though being polyesters alkaline conditions may lead to some hydrolysis).

The polymeric chain in the compounds of the invention will generally increase the molecular weight and size of the compounds as compared with e.g. alcohol ethoxylate surfactants. This may lead to useful properties as stabilisers at interfaces e.g. oil water interfaces, as in emulsions, because the molecules will be less easy to displace from the interface.

The compounds of the invention and particularly of the formula (I) can be made by reacting a precursor oligoester (or a reactive derivative) with a reactant which is either or both of a fatty monocarboxylic acid (or a reactive derivative) or a fatty alcohol (or a reactive derivative) under esterification conditions. The reactant chosen in any particular case used will depend on whether the precursor oligoester is bis-hydroxyl ended, mono-hydroxyl mono-carboxyl ended or bis-carboxyl ended. For bis-hydroxyl ended precursor oligoesters the reactant will be a carboxylic acid (or a reactive derivative) for bis-carboxyl ended precursor oligoesters the reactant will be an alcohol (or a reactive derivative) for mono-hydroxyl mono-carboxyl ended precursor oligoesters the reactant will be either a carboxylic acid (or a reactive derivative) or an alcohol (or a reactive derivative) when the desired product is the mono-ester and both such reactants when the desired product is the diester. As those skilled in the art will appreciate, it will often be the case that practical precursor oligoesters will be a mixture of two or possibly all three of the different end group types and the choice of subsequent reactant(s) may be determined by the particular mixture.

The invention accordingly includes a method of making a surfactant compound of the invention which comprises reacting a precursor oligoester (or a reactive derivative) with a reactant which is either or both of fatty monocarboxylic acid (or a reactive derivative) or a fatty alcohol (or a reactive derivative) under esterification conditions to form a fatty ester surfactant of the oligoester intermediate.

The invention particularly includes a method of making a compound of the formula (I) as defined above which comprises reacting a precursor oligoester (or a reactive derivative) with a reactant which is either or both of a $C_8$ to $C_{22}$ monocarboxylic acid (IV): $R^5COOH$, or a reactive derivative, or a $C_8$ to $C_{22}$ alcohol (V): $R^6OH$ (or a reactive derivative) under esterification conditions to form a fatty ester surfactant of the formula (I).

The oligoester precursor is typically of the formula (VI):

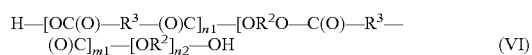

$$H—[OC(O)—R^3—(O)C]_{n1}—[OR^2O—C(O)—R^3—(O)C]_{m1}—[OR^2]_{n2}—OH \quad\quad (VI)$$

where
each $R^2$ and each $R^3$ are independently as defined for formula (I);
m1 is from 1 to 20, particularly from 3 to 10, more particularly from 3.5 to 8;
n1 is 0 or 1; and
n2 is 0 or 1
provided that n1 and n2 are not both 1.
If n1 and n2 were both 1 then in effect m1 would be reduced by 1.

Corresponding to the three sub groups of compounds of the invention as discussed above, the invention further includes:

a a method of making a surfactant compound of the invention which comprises reacting a bis-hydroxyl ended precursor oligoester (or a reactive derivative) with a fatty monocarboxylic acid (or a reactive derivative) under esterification conditions to form a fatty ester surfactant of the oligoester intermediate; particularly
  a method of making a compound of the formula (I) as defined above which comprises reacting a precursor oligoester of the formula (VIa below) as defined above (or a reactive derivative) with a $C_8$ to $C_{22}$ monocarboxylic acid (IV): $R^5COOH$ (or a reactive derivative) under esterification conditions to form a fatty ester surfactant of the formula (Ia).

b a method of making a surfactant compound of the invention which comprises reacting a mono-hydroxyl mono-carboxyl ended precursor oligoester (or a reactive derivative) with a fatty monocarboxylic acid (or a reactive derivative) and/or a fatty alcohol (or a reactive derivative) under esterification conditions to form a fatty ester surfactant of the oligoester Intermediate; particularly
  a method of making a compound of the formula (I) as defined above which comprises reacting a precursor oligoester of the formula (VIb below) as defined above (or a reactive derivative) with a reactant which is either or both of a $C_8$ to $C_{22}$ monocarboxylic acid (IV): $R^5COOH$ (or a reactive derivative) or a $C_8$ to $C_{22}$ alcohol (V): $R^6OH$ (or a reactive derivative) under esterification conditions to form a fatty ester surfactant of the formula (Ib); and c a method of making a surfactant compound of the invention which comprises reacting a bis-carboxyl ended precursor oligoester (or a reactive derivative) with a fatty alcohol (or a reactive derivative) under esterification conditions to form a fatty ester surfactant of the oligoester intermediate; particularly
  a method of making a compound of the formula (I) as defined above which comprises reacting a precursor oligoester of the formula (VIc below) (or a reactive derivative) with a reactant which is a $C_8$ to $C_{22}$ alcohol (V): $R^6OH$ (or a reactive derivative) under esterification conditions to form a fatty ester surfactant of the formula (Ic).

When the oligoester precursor is bis-hydroxy ended it will typically be of the formula (VIa):

$$H—[OR^2—OC(O)—R^3—(O)C]_m—[OR^2]—OH \quad\quad (VIa)$$

where $R^2$, $R^3$ and m are as defined above for formula (I); and will be reacted with an acid of the formula (IV), under esterification conditions, to make the compound of the formula (I).

The molar proportion of acid of the formula (IV) will usually be at least 1 mole per mole of hydroxyl in oligomer (VIa) that it is desired to esterify, generally 1 for a mono-ester and 2 for a di-ester. We have not generally found it necessary to use a significant molar excess of the monocarboxylic acid to promote formation of the ester product.

When the oligoester precursor is mono-hydroxy monocarboxy ended it will typically be of the formula (VIb):

and will be reacted with an acid of the formula (IV) or alcohol of the formula (V), under esterification conditions to make the compound of the formula (I). The molar proportion of acid and/or alcohol will usually be at least 1 mole per mole of hydroxyl in oligomer (VIb) that it is desired to esterify, generally 1 for a mono-ester and 2 for a di-ester (of course for the diester one of these moles will be derived from a monocarboxylic acid and one from an alcohol). We have not generally found it necessary to use a significant molar excess of the monocarboxylic acid to promote formation of the ester product.

When the oligoester precursor is bis-carboxy ended it will typically be of the formula (VIc):

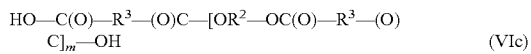

where $R^2$, $R^3$ and m are as defined above for formula (I); and will be reacted with an alcohol of the formula (V), under esterification conditions, to make the compound of the formula (I). The molar proportion of alcohol of the formula (V) will usually be at least 1 mole per mole of carboxyl in oligomer (VIc) that it is desired to esterify, generally 1 for a mono-ester and 2 for a di-ester.

Of course, the immediate resulting product will be a statistical mixture of mono-ester, di-ester and unreacted oligomer the proportions depending on the proportions of the oligomer and acid and the reaction conditions employed.

The precursor oligoesters of the formula (VIa), (VIb) and (VIc) can be made by reacting a polyol (III) and dicarboxylic acid (IV) under esterification conditions, particularly using a catalyst e.g. an alkali catalyst. The particular nature of the oligoester or the proportions of the oligoesters (VIa), (VIb) and (VIc) In a mixture will depend on the effective molar ratio of the starting polyol (II) and dicarboxylic acid (III) and the reaction conditions used in the esterification reaction. Where the starting materials include groups that may be susceptible to decarboxylation reactions e.g. malonic acid, or to branching reactions e.g. tricarboxylic acids such as citric acid (which may also be susceptible to decarboxylation) the use of relatively gentle oligomerisation (esterification) conditions can be useful to obtain the desired product. We have found that not adding a separate catalyst (the acid groups in the starting materials will provide some catalysis), while operating under relatively moderate elevated temperatures as is described below, can enable successful reactions with such materials, particularly malonic and citric acids, where the use of catalysts may in effect act to promote side reactions to an undesirable extent.

Especially where the polyol (II) has four or more carbon atoms and four or more hydroxyl groups, usually two primary hydroxyls and 2 or more secondary hydroxyls, it may be susceptible to react to form cyclic ethers. For example sorbitol can form sorbitan cyclic ethers which may react further to form the dicyclic diether iso-sorbide. This reduces the number of free hydroxyl groups and is thus generally undesirable, but may need to be taken into account in choosing the proportions of starting materials for making the intermediate oligoester. Where the intermediate oligomer is hydroxyl or predominantly hydroxyl ended, it may be desirable to use a molar excess of the polyol (II) to promote speedy polyesterification In making the intermediate, leaving unreacted polyol at this stage. We have not generally found it necessary to remove such unreacted polyol before the second stage reaction.

We have found that it is practical to make the compounds of the formula (I), by first making the oligoester (VI) by reaction of polyol (II) and dicarboxylic acid (III) under alkali catalysis and then further reacting the oligomer with carboxylic acid (IV) and or alcohol (V). The same reaction vessel may be used and it may not be necessary to separate or purify the oligomer, before further reaction. Using alkali derived from alkali metals e.g. sodium or potassium hydroxide or carbonate, particularly mild alkali such as carbonates, especially potassium carbonate, appears to be effective, particularly when making oligoesters that are hydroxyl ended e.g. the bis-hydroxyl ended oligoesters especially of the formula (Ia). Further such catalysts can be used for the further esterification and it is thus possible to use the same catalyst used in the oligomerisation. If required further catalyst may be added between the first and second stages of reaction.

In relation to the synthesis of the intermediate oligoesters, the present invention includes a method of making an oligoester which comprises reacting a polyol (or a reactive derivative) with a dicarboxylic acid (or a reactive derivative), under esterification conditions to form an oligoester.

In this aspect, the invention particularly provides a method of making an oligoester of the formula (VI) as defined above which comprises reacting a polyol of the formula (II): HO—$R^2$—OH, (or a reactive derivative) with a dicarboxylic acid of the formula (III): HOOC—$R^3$—COOH, (or a reactive derivative), under esterification conditions to form the oligoester. As is noted above the oligoesters can be bis-hydroxyl ended of the formula (VIa), bis-carboxyl ended of the formula (VIc), or mono-hydroxyl mono carboxyl ended of the formula (VIa).

Desirably the esterification conditions include:
a the use of an alkali catalyst, particularly a mild alkali catalyst, especially potassium carbonate; and/or
b a reaction temperature of from 100° C. to 200° C., more usually from 120° C. to 185° C. and desirably from 150° C. to 180° C., e.g. about 170° C.; and/or
c a reaction pressure which is subambient, particularly from 50 to 250 mBar (0.5 to 25 kPa) e.g. about 100 mBar (10 kPa).

In these reactions (making the oligoester intermediate or subsequent esterification to form the surfactant compounds) carboxylic acid functionality may be substituted by reactive derivatives such as lower e.g. $C_1$ to $C_6$, alkyl, particularly methyl or ethyl, esters, as in dialkyl esters of the dicarboxylic acid (III) or esters of the acid (IV) which may be glycerides such as triglycerides having residues of the fatty acid (IV), or anhydrides. We have successfully used acid anhydrides to make the intermediate oligoesters, but care may be needed when using anhydrides because they are relatively reactive and in making the oligomer they may react also with less reactive hydroxyl groups thus potentially leading to branched oligomers which are likely to form water Insoluble or intractable gels of little value as emulsifiers even after subsequent esterification. Even more reactive carboxylic acid derivatives such as acid halides will not generally be used for this reason. Where esters are used as the source of the carboxylic acids, the catalyst used may be an alkali as described above or a catalyst specifically for trans-esterification reactions e.g. titanate ester such as tetrabutyl titanate.

Particularly where the polyol used in making the oligoester intermediate has more than 3 hydroxyl groups e.g. where it has five or more hydroxyl groups, particularly on adjacent carbon atoms, the polyol may be liable to react such as by cyclising e.g. to form sorbitan from sorbitol, or pyrolysis, if heated sufficiently. Thus, when these materials are used, it is desirable to use temperatures that are lower that are typically in making carboxylic acid esters, particularly with relatively long chain acids. Typically, using such materials, the temperatures used will be at least 100° C., more usually at least 120° C. and desirably at least 150° C., but not more than 200° C., more usually not more than 185° C., particularly not more than 180° C., with reaction temperatures about 170° C., being particularly suitable. Such relatively mild esterification temperatures also appear to avoid or reduce the extent of reaction at secondary hydroxyl groups this minimising the degree of branching in the oligoester intermediate of side chain esterification in the surfactant compounds. The use of mildly subambient pressure e.g. from 50 to 250 mBar (0.5 to 25 kPa) e.g. about 100 mBar (10 kPa) can benefit reaction speed to make the use of such temperatures more practical.

If the materials produced by the synthesis are coloured, particularly by coloured impurities, then the level of colour may be reduced by treatment with activated carbon and/or by bleaching e.g. with hydrogen peroxide particularly in making products for personal care end use applications.

The compounds of this invention can be made to have a range of water and/or oil solubility and thus can be used as surfactants in water or oil based systems. In particular, the compounds of the invention may have HLB values in the range 4 to 18, including the relatively hydrophilic range 8 to 18 and the relatively oleophilic (hydrophobic) range 4 to 6.

Surfactants used in water based systems are generally water soluble, having an HLB greater than 7, particularly from 8 to 18. Such materials can be used as oil in water emulsifiers, particularly in personal care applications; as dispersants for pigments; as emulsifiers in emulsion polymerisation; as wetting agents in aqueous systems; as surfactants in domestic detergents, particularly in laundry formulations; in crop protection formulations particularly as adjuvants, dispersants and/or emulsifiers in agrochemical formulations; and other applications.

The properties of the surfactants of this invention also make them suitable as emulsifiers particularly in oil in water emulsions e.g. in personal care applications. Personal care emulsion products can take the form of creams and milks desirably and typically include emulsifier to aid formation and stability of the emulsion. Typically, personal care emulsion products use emulsifiers (including emulsion stabilisers) in amounts of about 3 to about 5% by weight of the emulsion. The oil phase of such emulsions are typically emollient oils of the type used in personal care or cosmetic products, which are oily materials which is liquid at ambient temperature or solid at ambient temperature, in bulk usually being a waxy solid, provided it is liquid at an elevated temperature, typically up to 100° C. more usually about 80° C., so such solid emollients desirably have melting temperatures less than 100° C., and usually less than 70° C., at which it can be included in and emulsified in the composition.

The concentration of the oil phase may vary widely and the amount of oil is typically from 1 to 90%, usually 3 to 60%, more usually 5 to 40%, particularly 8 to 20%, and especially 10 to 15% by weight of the total emulsion. The amount of water (or polyol, e.g. glycerin) present in the emulsion is typically greater than 5%, usually from 30 to 90%, more usually 50 to 90%, particularly 70 to 85%, and especially 75 to 80% by weight of the total composition. The amount of surfactant used on such emulsions is typically from 0.1 to 10%, more usually 0.5 to 8%, more desirably 1 to 7%, particularly 1.5 to 6%, and especially 2 to 5.5%, by weight of the emulsion.

The end uses formulations of such emulsions include moisturizers, sunscreens, after sun products, body butters, gel creams, high perfume containing products, perfume creams, baby care products, hair conditioners, skin toning and skin whitening products, water-free products, antiperspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes. A preferred formulation type is a sunscreen containing one or more organic sunscreens and/or inorganic sunscreens such as metal oxides, but desirably includes at least one particulate titanium dioxide and/or zinc oxide, The surfactants of this invention can be used as emulsifiers in emulsion polymerisation. Typically emulsion polymerisation is carried out on emulsions of ethylenically unsaturated monomers in water. Suitable monomers include unsaturated carboxylic acids and their alkyl esters, amides, N-substituted amides and nitriles, aromatic vinyl compounds, diene compounds which may be included as monomers or specifically as crosslinking agents, vinylethers, vinylesters, olefines and hydrophobic allyl compounds.

Such emulsion polymerisation methods are particularly applicable to the manufacture of acrylic copolymers, for example those where at least 50%, more usually at least 60%, desirably at least 80% e.g. 90% or more up to 100%, by weight of the monomers are acrylic monomers. The acrylic polymers may be those based on mixed alkyl acrylates, especially where the predominant monomer is methyl methacrylate, and may include anionic units such as (meth)acrylic acid units or cationic units such as amino substituted ethylenically unsaturated monomers.

The amount of surfactant used will depend on the particular monomers and the polymerisation system used, the degree of colloidal stability needed and the desired particle size of the polymer in the product latex. For an otherwise conventional oil in water emulsion polymerisation, to give a latex having a particle size of from 80 to 500 nm the amount of surfactant used will typically be from 0.25 to 5 parts by weight surfactant per 100 parts by weight total monomer (phm). More usually the amount will be from 0.5 to 2.5 phm, particularly from 1 to 2 phm.

In microemulsion polymerisation systems, the concentration of monomer is typically substantially lower than in conventional emulsion or other dispersion polymerisation systems e.g. from 3 to 10% by weight. The proportion of surfactant relative to the amount of monomer is also relatively high because the microemulsion has higher interface area per unit mass of monomer corresponding to the smaller emulsion particle size and typical levels can be from 10 to 150 phm. Overall solids contents of microemulsion systems are usually in the range 15 to 30% by weight of the total emulsion.

The surfactants of this invention can be used as dispersants for solids in aqueous media, particularly for pigments, including inorganic pigments e.g. titanium dioxide, pigmentary iron oxide and organic pigments e.g. phthalocyanine pigments, carbon black, and similar materials. The amount of surfactant used in such dispersant applications depends on the materials employed and the dispersion concentration required, but is usually from 0.2 to 10% by weight of the solid e.g. pigment being dispersed. In aqueous dispersions, for inorganic pigments the amount used is typically from 0.05 to 5%, more usually 0.1 to 2.5%, by weight of the solid dispersed and for organic pigments typically the amount used is from 3 to 10% by weight of the solid dispersed. Typical such dispersions will contain up to about 70%, often up to about 65%, of inorganic pigment and up to about 35% by weight organic pigment, but this may be up to 50% for pigment pastes. When incorporated into end use products such as paints typical pigment levels in the final product will be about 3 to about 30%, particularly about 20 to about 25%, for inorganic pigments, about 1 to about 15% for organic pigments, particularly about 10 to about 12%, especially for phthalocyanine type organic pigments, and about 0.5 to about 5%, particularly about 3 to about 3%, for carbon black. The continuous phase in such dispersions will usually be water based.

The surfactants can also be used as domestic detergents for example in laundry applications and may be used alone or in combination with other, non-ionic, anionic, cationic, amphoteric and/or zwitterionic surfactants. Formulations including surfactants of this invention for laundry use will typically also include further components including one or more of builders e.g. phosphates, particularly sodium tripolyphosphate; organics such as citrate and/or tartrate; and/or zeolites; flow and/or filter aids, commonly used in powder formulations, which may include co-builders such as sodium carbonate and/or bicarbonate, particularly in powders where the builder is a zeolite (though because typical co-builders are alkali, they will not usually be used in hand washing formulations); corrosion inhibitors; anti-redeposition aids such as carboxy methyl cellulose; and optical brighteners. Further components may include perfumes; enzymes, including lipases, proteases, cellulases and/or amylases; bleaches, typically based on sodium perborate, sodium percarbonate or similar materials, which will typically be used with bleach activators such as tetra-acetyl ethylene diamine (TAED); and stabilisers such as phosphonates or ethylene diamine tetra-acetic acid (EDTA) usually as the sodium salt; soaps; foam control agents (often soaps) and fabric conditioners (softeners) such as quaternary ammonium salts and amine oxides which may be coated onto bentonite type clays.

The compounds of the invention can used as surfactants in agrochemical formulations, in particular as adjuvants for example with herbicides, fungicides, insecticides, acaricides and plant growth regulator formulations, dispersants and/or emulsifiers. The amount of surfactant used to disperse agrochemical(s), is typically at a concentration of 1 to 30% based on the formulation and used as adjuvants, a concentration of from 5 to 60% based on concentrate formulations and 1 to 100% in or as components for addition to tankmixes. Other conventional components can be included in such formulations such as oils e.g. mineral oil(s), vegetable oil(s) and alkylated vegetable oil(s); solvents and/or diluents; and other surfactants which may be anionic surfactants, cationic surfactants or non-ionic surfactants. Such other components will, as with formulations using purely conventional surfactants, be used in amounts based on the desired effect.

The surfactants of the invention can also be used in oilfield applications e.g. as foaming agents in foam drilling, as kinetic gas hydrate inhibitors and as water based drilling fluid lubricants.

Foam drilling fluids are water based drilling fluids in which the water phase is foamed e.g. to minimise formation damage of water sensitive formations. As foaming agents in foam drilling fluids the amount of the surfactant used will typically be from 1 to 3%, more usually from 1 to 2%, by weight of the drilling fluid.

Kinetic gas hydrate inhibitors are materials added to water containing hydrocarbon, particularly C1 to C4 hydrocarbon alkane containing streams to slow down gas hydrate formation or to modify the crystal form of the gas hydrate so as to reduce crystal agglomeration which otherwise would lead to pipe or similar blockage. In gas hydrate inhibition, the surfactants will typically be used at from 0.05 to 5% by weight based on the water phase of the stream being treated.

The surfactant compounds of the invention may be used to provide enhanced lubricity in water based drilling fluids. In use in this application the amount of surfactant used will typically be from 0.05 to 10% by weight of the fluid.

Surfactants used in oil based systems are generally oil soluble and usually water insoluble and in particular having an HLB of less than 7, more usually from 4 to 6. Such materials can be used as emulsifiers and/or stabilisers for water in oil emulsions; or as dispersants for solids in non-aqueous liquids. As such they can be used in a wide variety of applications including in: (water in oil) emulsion polymerisations, particularly to make polyacrylamide (PAM) or related polymers by free radical inverse emulsion polymerisation (i-PAM); emulsion explosives; in water in oil cosmetic emulsions; agrochemical, particularly plant growth regulator, herbicide, and/or pesticide, emulsions dispersions and suspoemulsions; and as emulsifiers and/or dispersants; dispersions of solids, such as pigments and/or inert inorganic metal salts, especially in organic media; oilfield drilling fluid additives, particularly as dispersants and/or emulsifiers for drilling muds and invert emulsion drilling fluids; metal working applications particularly in rolling oil emulsions and cutting fluids.

The surfactants of the invention can be used as emulsifiers in i-PAM polymerisation, in which acrylamide and any co-monomer(s), are dissolved in water, this solution is emulsified in oil, using surfactants as emulsifiers and stabilisers, and the polymerisation initiated. The result is a dispersion of water droplets, containing dissolved PAM, in the oil. Although the viscosity of the aqueous PAM solution is high, the effective viscosity of the emulsion is determined primarily by the oil continuous phase, chosen to be suitably low. In use e.g. in water treatment, the emulsion has to be broken, usually by inverting on dilution into water. The surfactant system must provide adequate emulsion stability before, during and after (for storage) polymerisation, but permit ready breaking of the emulsion during inversion on dilution into water, to facilitate rapid release of the polyacrylamide polymer into the water phase in which it will act. Inversion is commonly promoted by the addition of hydrophilic surfactants after the polymerisation. Relatively oleophilic surfactants of the invention can be used to emulsify and/or stabilise the water in oil emulsion used in this type of polymerisation process.

In i-PAM, the oil phase is typically a mineral oil, particularly a paraffin oil, or an ester oil and the amount of emulsifier surfactant used is typically from 2.5 to 7%, usually from 3 to 4%, by weight of the polymerisation emulsion. The emulsifier system will typically combine a polymeric surfactant, particularly including a surfactant of invention especially of the formula (I), and a low molecular weigh low HLB surfactant (relatively less effective as an emulsion stabiliser so that the stabilisation of the emulsion is not so good that inversion is difficult)—the low molecular weight enables it to readily diffuse away from the phase interface during inversion. Commonly the low molecular weight surfactants are fatty acid monoglycerides, fatty acid sorbitan esters or similar surfactants. The relative proportions by weight of polymeric surfactant to low HLB low molecular weight surfactant is typically from 5:95 to 50:50 more usually from 10:90 to 40:60 and commonly about 15:85 to 30:70.

Oleophilic types of surfactants of this invention can also be used in dispersing solids, particularly pigments such as those described above, in non-aqueous media such as white spirit or aromatic media. In such uses the amount of surfactant used will typically be from 0.5 to 7.5%, more usually from 1 to 5%, by weight of the dispersion.

The compounds of the invention are also useful as emulsifiers or emulsion stabilisers in emulsion explosives in which an oxidiser, typically an aqueous solution of an oxidiser salt usually nitrates, is emulsified in a liquid fuel, typically a hydrocarbon fuel such as mineral and/or paraffin oil, which may also include other petroleum components e.g. microcrystalline wax, paraffin wax, slack wax, and/or petroleum refining distillation residues. The oxidiser solution is usually a saturated or supersaturated aqueous solution, of nitrate salts, particularly $NH_4NO_3$, alkali metal nitrates or alkaline earth metal nitrates, optionally with minor proportions of other salts e.g. $NH_4Cl$ and typically contains 40% to 70% by weight ammonium nitrate and 20% of other nitrates. The internal oxidiser phase is typically at least 75% more usually more than 90% e.g. about 95%, by volume of the emulsion explosive. For use, emulsion explosives typically also include additives to sensitise the compositions to detonation. Commonly this is done by adding materials that provide solid surfaces e.g. solid $NH_4NO_3$, especially as prills, or gas filled voids e.g. by including sodium nitrite, which produces gas by chemical reaction, or glass microspheres, which provide physical voids.

The compounds of the invention particularly of the formula (I) can be used as emulsifiers alone or in combination with other typically oil soluble emulsifiers particularly sorbitan fatty acid esters such as sorbitan mono oleate (SMO); phospholipids such as soyalecithin or oxazoline or imidazoline derivatives thereof; PIBSA alkanolamine reaction products; or fatty acid condensation products with polyethylene glycols. The total amount of emulsifier used in emulsion explosives is typically from 0.5 to 5%, more usually from 1 to 4%, by weight based on the overall emulsion. Desirably, the proportion of emulsifier of the formula (I) is at least 50%, more usually at least 75%, by weight of the total emulsifier used in the emulsion explosive.

The compounds of the invention can be used as water in oil dispersants and/or emulsifiers in personal care and cosmetic applications, in particular, in formulations including relatively high concentrations of solutes in a dispersed hydrophilic phase and in the manufacture of multiple emulsions. The oil phase used in this aspect of the invention is typically an emollient oil which may be liquid or solid at ambient temperature.

The discontinuous, usually aqueous, phase can be water or a water based liquid, or a hydrophile phase which can be a solution in water of the hydrophilic material or the discontinuous phase can, in certain cases, be a substantially water free liquid phase of the hydrophilic material. In such systems the surfactant of the invention is typically used in an amount of 0.5 to 5%, more usually from 1 to 2%, by weight of the total emulsion.

The surfactants of this invention can be used as emulsifiers and/or dispersants in agrochemical applications. The invention accordingly includes an agrochemical emulsion or dispersion, in which at least one surfactant compound of the invention, particularly of the formula (I), is included as an emulsifier or dispersant. Within this, more particularly the invention includes:

i an agrochemical emulsion including an agrochemically active material which is dissolved, dispersed or emulsified in a first liquid component, the first liquid component being emulsified in a second liquid component;

ii an agrochemical formulation including an agrochemically active material which is dissolved, dispersed or emulsified in a first liquid component, a second liquid component being emulsified in the first liquid component;

iii an agrochemical dispersion in which a solid component is dispersed in a liquid phase.

The agrochemically active material(s) included in the emulsions and/or dispersions in this aspect of the invention can include one or more plant growth regulators, herbicides, and/or pesticides, for example insecticides, fungicides, acaricides, nematocides, miticides, rodenticides, bactericides, molluscicides and bird repellants. Examples of classes of actives include: Herbicides: including water soluble, particularly non-selective, herbicides, particularly N-phosphonomethyl glycine herbicides e.g. Glyphosate and Sulfosate, and the glufosinate and bipyridyl types of non-selective herbicides, triazines, substituted ureas, sulphonyl ureas, pyridine carboxylic acids, aryloxy alkanoic acids, 2-(4-aryloxy-phenoxy)propionic acids, bis-carbamates; Fungicides: including thiocarbamates, particularly alkylenebis(dithiocarbamate)s, strobilurins, dicarboximides, benzimidazoles, azoles, inorganic fungicides; insecticides including benzoyl ureas; and Acaricides including tetrazines.

Particular applications of the polymeric surfactants of the invention in agrochemicals include:

Concentrated emulsions which contain both aqueous and non-aqueous phases with the continuous phase usually being aqueous.

Oil in water agrochemical emulsions are generally non-transparent white emulsions which are applied after further dilution in the spray tank.

Water in oil emulsions which are generally non-transparent (white) emulsions and are typically commercialised as ready to use formulations, ultra low volume systems, and other specialty applications.

Dispersions, in an aqueous or oil based liquid, of solid components which commonly will be insoluble actives, particularly fungicides or herbicides, but may be non-agrochemically active insoluble solid components.

Suspoemulsions which are systems in which at least one liquid and at least one solid disperse phase is included in a continuous phase, which is usually aqueous.

Combination formulations, particularly concentrated dispersions in which the compounds of the formula (I) can be used as dispersants in formulations which combine agrochemicals having different physical forms or presentations in formulation and/or different activities.

In agrochemical compositions, the surfactants of the invention, particularly of the formula (I), can be used alone or in combination with other polymeric surfactants, but desirably, the proportion of surfactant of the invention, particularly of the formula (I), is at least 50%, more usually at least 75%, by weight of the total polymeric surfactant used as emulsifier and/or stabiliser and/or dispersant in the composition.

One area of practical importance in this aspect of the invention is sunfilters and sunscreens or other cosmetics containing sunfilter and/or sunscreen components. The sunfilters or sunscreens can be physical sunscreens such as those based on titanium dioxide e.g. ultra-fine titanium dioxide, or zinc oxide, which are understood to act by strongly scattering ultraviolet radiation, or chemical sunfilters or sunscreens such as compounds that absorb ultraviolet radiation, particularly UVB and UVA sunscreen agents. The amount of sunfilters and/or sunscreen used will depend on the properties of the materials used, but typically for physical sunscreens the amount will be 0.1% to 5%, more usually from 0.25 to 2.5%, by weight of the overall emulsion and for chemical sunfilters and/or sunscreens 0.05 to 3%, more usually from 0.1 to 1.5%, by weight of the overall emulsion. Depending on their nature the sunfilter and sunscreen components may be present in the generally aqueous discontinuous phase or in the oil continuous phase or in both phases. Particularly where the sunscreens is a physical sunscreen, the overall emulsion will be combined suspension and emulsion and these are commonly referred to as suspoemulsions (see further below).

Suspoemulsions are a further important area in this aspect of the invention. They are briefly referred to above in connection with sunscreens, but other solid components can be included such as pigments as are often included in make up cosmetics. When pigments are used, they may be pigments organic or inorganic and may be present in the oil phase, particularly for organic pigments and hydrophobic inorganic pigments, or in the present in the water phase, particularly for hydrophilic Inorganic pigments, or in both phases, when used are typically present in concentrations of from 0.5 to 20% more usually from 1 to 10%, by weight of the emulsion.

Generally the amount of the compound of the formula (I) used in cosmetic compositions of this aspect of the invention is from 0.5 to 7%, more usually from 1 to 5%, by weight of the formulation. The compound of the formula (I) can be used alone or in combination with other polymeric emulsifiers, but desirably, the proportion of the compound of the formula (I) is at least 50%, more usually at least 75%, by weight of the total emulsifier used in stabilising the cosmetic emulsion.

The surfactant compounds of the invention may also be used as demulsifiers in oilfield applications. Demulsifiers are typically used to aid separation of water emulsified in the hydrocarbon phase of oils. In use as demulsifiers, the amount of surfactant used as a demulsifier will typically be from 1 to 500 ppm, particularly from 5 to 150 ppm, by weight of the oil stream.

The surfactant compounds of the invention may also be used as emulsifiers and/or lubricants in metal working applications particularly in rolling oil emulsions and cutting fluids.

The compounds of the invention can further be used as dispersants finely divided solids in non-aqueous fluids, particularly liquid organic media. Examples of such materials include pigments, particularly for paints and solvent inks; dyes including disperse dyes; magnetic metal oxides; extenders and fillers; optical brightening agents; and textile auxiliaries; solids for oil based and invert emulsion drilling muds; dirt and solid particles in dry cleaning fluids; and magnetic materials for magnetic recording media. The medium is typically an oil such as a hydrocarbon or A natural or synthetic ester oil, or a coating composition resin such as an alkyd resin, or special mixture of glycols typically used in the preparation of multi-purpose pigment pastes or pigment concentrates. Such dispersions typically contain from 5 to 95%, more usually from 10 to 60%, and especially from 20 to 50%, by weight of the solid, depending on the nature of the solid and the relative densities. The dispersion may be made by conventional method for making dispersions.

The following Examples illustrate the invention. All parts and percentages are by weight unless otherwise stated.

| Materials | |
|---|---|
| Polyols | |
| PC6a | sorbitol (100% active) |
| PC6b | sorbitol (70 wt % aqueous solution) |
| PC3 | glycerol (100% active) |
| PC5 | xylitol (100% active) |
| PC3/C6 | glycerol sorbitol mixture (1:3 molar ratio) |
| Di-acids | |
| DAC6 | adipic acid |
| DADMA | dimethyl adipate |
| DAC4 | succinic acid |
| DAC8 | suberic acid |
| DAC10 | sebacic acid |
| DAC5 | glutaric acid |
| Mono-acids | |
| MAC8 | octanoic acid |
| MAC12 | lauric acid—Prifac 2922 ex Uniqema |
| MAcofa | coconut oil fatty acids (mainly $C_{12}$) |
| MAC16 | palmitic acid |
| MAC18 | stearic acid |
| MAC18i | iso-stearic acid (a mixture of $C_{14}$ to $C_{22}$ fatty acids averaging about $C_{18}$) |
| Catalysts | |
| Cat1 | $K_2CO_3$ |
| Cat2 | NaOH |
| Oils | |
| Oil1 | iso-hexadecane oil (Arlamol HD ex Uniqema) |
| Surfactants | |
| Surf1 | stearyl alcohol 20 ethoxylate (Brij 78 ex Uniqema) |

Test Methods

Acid Value (AV) was measured by the method of ASTM D1980-87.

Emulsion Stability

Oil in water emulsions (1% w/w emulsifier, 20% w/w oil) were prepared by weighing 158 g of demineralised water into a 400 ml tall form beaker, adding 2 g of test emulsifier and stirring the mixture using a magnetic flea and hotplate/stirrer at room temperature until completely dissolved. 40 g of Oil 1 were then added to the aqueous solution and the mixture homogenised using an Ultra Turrax T25 blender at 11000 rpm (ca 183 Hz) for 2 mins. The resultant emulsion was transferred to two 50 ml volumetric cylinders, one of which was stored at room temperature (Amb) and the other in a hotbox at 50° C. The emulsion mean droplet size (in μm) of the stored samples was measured using a Coulter Multisizer II after 1 day (1 D), 1 week (1 W), and 1 month (1 M).

SYNTHESIS EXAMPLES

Example SE1

Poly(Sorbitol Adipate)Laurate

Anhydrous sorbitol (182 g; 1 mol), adipic acid (87.6 g; 0.6 mol) and potassium carbonate (9.66 g; 7 mol % based on sorbitol) were charged to a 250 ml round bottomed flask fitted with a propeller stirrer, side-arm water condenser and collection flask, vacuum pump, nitrogen sparge and thermometer (thermocouple) and on an isomantle. The mixture was heated under stirring (200 rpm) to distil off free water (mostly at below 130° C.); vacuum (100 mbar) was then applied and the temperature was increased to 170° C. and held until the acid value of the mix was <5 mg KOH.g$^{-1}$ (normally 3 to 4 hrs). The vacuum was then released and molten lauric acid (30.1 g; 0.15 mol) at ca. 90° C. was added. Vacuum (500 mbar) was re-applied and the mix stirred (300 rpm) with the nitrogen sparge until the acid value was <5 mg KOH.g$^{-1}$ (normally after ca, another 3 to 4 hours); the vacuum was then released and the product discharged.

The structure of the product was confirmed using MALDI mass spectrometry and gel permeation chromatography.

Further esters of oligopolyol esters were made by the general method set out in Example SE1 but making changes to the starting materials, material proportions or conditions. Table 1a below (including SE1 for completeness) sets out the diacid and other materials used and reaction conditions for the oligomerisation esterification and Table 1b the monoacid and reaction conditions for the second stage esterification together with some information on the properties of the products made. In these tables, the molar % figures are based on the polyol used.

In making these compounds variations of the synthetic route described in Example SE1 were also used. In particular anhydrous sorbitol could be substituted for the aqueous sorbitol used in SE1 and for materials including succinic acid residues succinic anhydride could be used instead of succinic acid e.g. using the following procedure:

200 g anhydrous sorbitol (1.10 mol), 65.9 g (0.66 mol) succinic anhydride and 11.5 g (7.5 mol % based on sorbitol) potassium carbonate were charged to a 500 ml round bottomed flask equipped as in SE1. The mixture was heated under stirring (200 rpm) to 140° C. After 30 mins at this temperature, a sample was taken for FT-IR analysis (to confirm the absence of anhydride). The temperature was increased to 165° C. and a vacuum (100 mbar) was applied. The reaction was maintained under these conditions until the acid value of the reaction mix was <5 mg KOH.g$^{-1}$ (normally 3 to 4 hrs). The vacuum was released and the product discharged.

Using these methods the products were very similar to corresponding compounds made using the method of SE1.

TABLE 1b

| Ex No | Monoacid type | mol[1] | Temp (° C.) | Press (mbar) | Time (hr) | AV | Notes |
|---|---|---|---|---|---|---|---|
| SE1 | MAC12 | 0.25 | 173 | atm | 3.5 | 4.5 | clear—1 phase |
| SE2 | MAC12 | 0.25 | 171 | atm | 9.3 | 4.5 | clear—1 phase |
| SE3 | MAC12 | 0.35 | 174 | atm | 7.3 | 4.3 | clear—1 phase |
| SE4 | MAC12 | 0.25 | 177 | atm | 19 | 2.5 | clear—1 phase |
| SE5[2] | MAC12 | 0.25 | 174 | atm | 9.0 | 3.8 | cloudy 2 phase mixture |
| SE6[2] | MAC12 | 0.25 | 183 | atm | 18.5 | 9.2 | cloudy 2 phase mixture |
| SE7 | MAC12 | 0.25 | 170 | 500 | 6.5 | 4.7 | clear—1 phase |
| SE8 | MAcofa | 0.25 | 182 | atm | 20.0 | 5.9 | cloudy 2 phase mixture |
| SE9 | MAi-C18 | 0.25 | 200 | atm | 16.0 | 7.3 | cloudy 2 phase mixture |
| SE10 | MAC16 | 0.25 | 180 | 400 | 13.0 | 6.8 | cloudy 2 phase mixture |
| SE11 | MAC12 | 0.25 | 170 | 500 | 4 | 4.3 | clear—1 phase |
| SE12 | MAC12 | 0.25 | 170 | 500 | 5 | 3.3 | clear—1 phase |
| SE13 | MAC12 | 0.25 | 170 | 500 | 3 | 4.6 | clear—1 phase |
| SE14 | MAC8 | 0.25 | 170 | atm | 7.5 | 8 | clear—1 phase |
| SE15 | MAC8 | 0.25 | 170 | atm | 9 | 13.8 | clear—1 phase |
| SE16 | MAC12 | 0.25 | 170 | 500 | 3 | 4.7 | clear—1 phase |
| SE17 | MAC12 | 0.20 | 170 | 500 | 3 | 4.8 | clear—1 phase |
| SE18 | MAC12 | 0.25 | 170 | 500 | 4 | 12.3 | cloudy—2 phase |
| SE19 | MAC12 | 0.25 | 170 | 500 | 4.5 | 2.3 | clear—1 phase |
| SE20 | MAC12 | 0.25 | 170 | 500 | 5.3 | 4.1 | clear—1 phase |
| SE21 | MAC12 | 0.25 | 170 | 500 | 4 | 3.9 | clear—1 phase |
| SE22 | MAC18 | 0.15 | 170 | 500 | 6 | 4.2 | clear—1 phase |

[1]molar ratios/percentages based on sorbitol
[2]lauric acid added after 8 hours of oligomerisation reaction
[3]glycerol:sorbitol—0.25:0.75 molar ratio TABLE 1a

| Ex No | Polyol | Diacid type | mol[1] | Catalyst type | mol %[1] | Temp (° C.) | Press (mbar) | Time (hr) | AV |
|---|---|---|---|---|---|---|---|---|---|
| SE1 | PC6a | DAC6 | 0.6 | K$_2$CO$_3$ | 7.5 | 173 | atm | 3.5 | 4.7 |
| SE2 | PC6a | DAC6 | 0.7 | K$_2$CO$_3$ | 7.5 | 171 | atm | 9.7 | 4.9 |
| SE3 | PC6a | DAC6 | 0.6 | K$_2$CO$_3$ | 7.5 | 174 | atm | 9 | 4.9 |
| SE4 | PC6a | DAC6 | 0.6 | NaOH | 7.0 | 168 | atm | 13 | 4.8 |
| SE5[2] | PC6a | DADMA | 0.6 | K$_2$CO$_3$ | 7.5 | 159 | atm | 8 | n/a |
| SE6[2] | PC6a | DAC4 | 0.6 | K$_2$CO$_3$ | 7.5 | 165 | atm | 12.5 | 9.2 |
| SE7 | PC6b | DAC6 | 0.6 | K$_2$CO$_3$ | 7.5 | 170 | 100 | 4.5 | 4.4 |
| SE8 | PC6a | DAC6 | 0.6 | K$_2$CO$_3$ | 7.5 | 170 | 100 | 3.5 | 5.9 |
| SE9 | PC6a | DAC6 | 0.6 | K$_2$CO$_3$ | 7.5 | 170 | 100 | 2.0 | 7.3 |
| SE10 | PC6a | DAC6 | 0.6 | K$_2$CO$_3$ | 7.5 | 170 | 100 | 2.0 | 6.8 |
| SE11 | PC6a | DAC8 | 0.6 | K$_2$CO$_3$ | 7.5 | 170 | 100 | 2.5 | 3.9 |
| SE12 | PC6a | DAC10 | 0.6 | K$_2$CO$_3$ | 7.5 | 170 | 100 | 3 | 4.6 |
| SE13 | PC6a | DAC6 | 0.6 | K$_2$CO$_3$ | 7.5 | 170 | 100 | 3 | 3.9 |
| SE14 | PC6a | DAC5 | 0.6 | K$_2$CO$_3$ | 7.5 | 170 | 100 | 2 | 4.6 |
| SE15 | PC6a | DAC4 | 0.6 | K$_2$CO$_3$ | 7.5 | 170 | 100 | 3 | 6.2 |
| SE16 | PC6a | DAC8 | 0.6 | K$_2$CO$_3$ | 7.5 | 170 | 100 | 2.5 | 5.1 |
| SE17 | PC6b | DAC6 | 0.6 | K$_2$CO$_3$ | 7.5 | 170 | 100 | 4.5 | 2.6 |
| SE18 | PC3 | DAC4 | 0.6 | K$_2$CO$_3$ | 7.5 | 170 | 100 | 4.0 | 4.2 |
| SE19 | PC3 | DAC6 | 0.6 | K$_2$CO$_3$ | 7.5 | 170 | 100 | 4.5 | 2.4 |
| SE20[3] | PC3/PC6b | DAC6 | 0.6 | K$_2$CO$_3$ | 7.5 | 170 | 100 | 5.2 | 2.9 |
| SE21 | PC5 | DAC6 | 0.6 | K$_2$CO$_3$ | 7.5 | 170 | 100 | 4.0 | 3.9 |
| SE22 | PC6b | DAC10 | 0.6 | K$_2$CO$_3$ | 7.5 | 170 | 100 | 4.0 | 4.5 |

Application Examples

Application Example AE1

Test oil in water emulsions were made up using the following general emulsion formulation:

| Material | amount (wt %) |
|---|---|
| surfactant | 1 |
| Oil 1 | 20 |
| salt | 0 or 3 |
| water | to 100 |

These emulsions were tested for stability as described above and the results are as set out in Table 2 below.

TABLE 2

| Ex No | Surfactant Type | Salt Conc (wt %) | Emulsion Stability (mean droplet size in µm) | | | | | |
|---|---|---|---|---|---|---|---|---|
| | | | Amb 1D | Amb 1W | Amb 1M | 50° C. 1D | 50° C. 1W | 50° C. 1M |
| AE1C.a | Surf1 | 0 | 7.8 | 8.9 | 9.0 | 7.8 | 8.9 | 8.9 |
| AE1C.b | Surf1 | 3 | 7.8 | 8.9 | 9.0 | 7.8 | 8.9 | 8.9 |
| AE1.1.a | SE4 | 0 | 8.7 | 10.2 | 10.0 | 8.7 | 9.9 | 9.4 |
| AE1.1b | SE4 | 3 | 8.7 | 10.2 | 10.0 | 8.7 | 9.9 | 9.4 |
| AE1.2.a | SE5 | 0 | 9.5 | 9.0 | 8.7 | 9.5 | 10.6 | 9.3 |
| AE1.2b | SE5 | 3 | 9.5 | 9.3 | 8.7 | 9.5 | 10.6 | 9.3 |
| AE1.3.a | SE6 | 0 | 9.0 | 8.4 | 7.8 | 9.0 | 10.8 | 8.9 |
| AE1.3b | SE6 | 3 | 9.0 | 8.4 | 7.8 | 9.0 | 10.8 | 9.0 |
| AE1.4 | SE21 | 0 | 9.2 | 9.3 | 9.2 | 9.4 | 9.3 | 9.1 |
| AE1.5 | SE23 | 0 | 6.0 | 6.0 | 5.9 | 6.0 | 6.0 | 6.2 |
| AE1.6 | SE24 | 0 | 6.2 | 6.8 | 6.8 | 6.4 | 6.6 | 8.4 |
| AE1.7 | SE25 | 0 | 9.8 | 9.9 | 9.9 | 9.4 | 9.5 | 10.4 |
| AE1.8 | SE26 | 0 | 9.8 | 9.6 | 9.7 | 9.7 | 9.8 | 9.8 |
| AE1.9 | SE32 | 0 | 9.6 | 9.8 | 9.6 | 9.8 | 9.8 | 9.8 |

The invention claimed is:

1. A surfactant compound of formula (I), comprising:

$$R^1-[OR^2O-C(O)-R^3-(O)C-]_m-R^4 \quad (I)$$

wherein
$R^1$ is H, a group $R^5(O)C-$, or a group $R^6O-[C(O)-R^3-(O)C]-$;
each $R^2$ is independently a $C_3$ to $C_{10}$ hydrocarbyl group including at least 1 substituent free hydroxyl group;
each $R^3$ is independently a $C_1$ to $C_{20}$;
$R^4$ is $-OH$, $-OM$ where M is a salt forming metal, an amine or ammonium group, a group $-OROR^6$, or a group $-OR^2O-R^7$;
$R^5$ is a $C_7$ to $C_{21}$ aliphatic hydrocarbyl group;
each $R^6$ is independently a $C_8$ to $C_{22}$ aliphatic hydrocarbyl group;
$R^7$ is H or a group $-C(O)R^5$ where $R^5$ is independently as defined above; and
m is from 3 to 20;
provided that at least one of $R^1$ and $R^4$ is or includes a group including a $C_7$ to $C_{21}$ hydrocarbyl group;
wherein:
i) the surfactant compound comprises a mono- or di-ester derived from the esterification of a fatty acid or fatty alcohol and an oligoester;
i) the oligoester is formed from a dicarboxylic acid and a polyol comprising primary and at least one secondary alcohol; and
ii) the mono- or di-ester comprises at least one free hydroxyl group that is at least one said secondary alcohol.

2. The compound of claim 1, wherein the compound comprises:
a) a fatty acid mono- and bis-ester of a bis-hydroxyl ended oligoester intermediate, of the formula (Ia):

$$R^{1a}-[OR^2O-C(O)-R^3-(O)C-]_m-OR^2O-R^{4a} \quad (Ia)$$

where
each $R^2$, each $R^3$ and m are independently as defined in claim 1 for formula (I);
$R^{1a}$ is a group $R^5(O)C-$; and
$R^{4a}$ is $-H$, or a group $-C(O)R^5$;
where each $R^5$ is independently as defined in claim 1 for formula (I); or b) a fatty acid or fatty alcohol mono- and fatty acid fatty alcohol bis-ester of a hydroxyl carboxyl ended oligoester intermediate, of the formula (Ib):

$$Ri^b-[OR^2O-C(O)-R^3-(O)C-]_m-R^{4b} \quad (Ib)$$

each $R^2$, each $R^3$ and m are independently as defined in claim 1 for formula (I);
$R^{1b}$ is H or a group $R^5(O)C-$;
$R^{4b}$ is $-OH$, $-OM_1$ where M is a salt forming metal or amine or ammonium group, or a group $-OR^6$;
where each $R^5$ and $R^6$ is independently as defined in claim 1 for formula (I), provided that at least one of $R^{1b}$ and $R^{4b}$ is or includes a $C_8$ to $C_{22}$ group; or
c) a fatty alcohol mono- or bis-ester of a bis-carboxyl ended oligoester intermediate, of the formula (Ic):

$$R^{1c}-[OR^2O-C(O)-R^3-(O)C-]_m-OR^{4c} \quad (Ic)$$

each $R^2$, each $R^3$ and m are independently as defined in claim 1 for formula (I);
$R^{1c}$ is a group $R^6O-C(O)-R^3-(O)C-$; and
$R^{4c}$ is H or a salt forming metal or amine or ammonium group or a group $-OR^6$;
where each $R^6$ is independently as defined in claim 1 for formula (I).

3. The compound of claim 1, wherein the group $R^2$ contains from 1 to 6 free hydroxyl groups.

4. The compound of claim 1, wherein the group $R^2$ is a group of the formula:

$$-(CH_2)_{p1}(CHOH)_{p2}(CH_2)_{p3}-$$

where p1 and p3 are each independently from 1 to 3, and p2 is from 1 to 6.

5. A compound as claimed in claim 4 wherein p1 and p3 are each 1, and p2 is 4.

6. The compound of claim 1, wherein the group $R^3$ is a group $-(CH_2)_n-$, where n is from 2 to 10.

7. A compound as claimed in claim 6 wherein n is 4.

8. The compound of claim 1, wherein the group $R^5$ is a $C_7$ to $C_{17}$, alkyl, alkenyl or alkadienyl group and the group $R^6$ is a $C_8$ to $C_{18}$ alkyl, alkenyl or alkadienyl group.

9. The compound of claim 6, wherein m is from 3.5 to 10.

10. An emulsion including the compound of claim 1 as an emulsifier.

11. The emulsion as claimed in claim 10 in the form of a oil in water personal care emulsion in which a disperse oil phase is an emollient oil or wax.

12. The emulsion of claim 11 in the form of a cream or a milk and including from 3 to 5% by weight of the emulsion of emulsifier and/or emulsion stabiliser.

13. A dispersion of a solid in an aqueous medium, wherein the solid phase of said dispersion comprises 0.2 to 10% by weight of the compound of claim 1.

14. A laundry detergent formulation including the compound of claim 1.

15. An agrochemical formulation including the compound of claim 1 as an adjuvant, dispersant and/or emulsifier.

16. A foam drilling fluid including from 1 to 3% by weight of the drilling fluid of the compound of claim 1 as a foaming agent.

17. A water based drilling fluid including from 0.05 to 10% by weight of the drilling fluid of the compound of claim 1 as a lubricating agent.

18. A dispersion of a solid in a non-aqueous medium, wherein the solid phase of said dispersion comprises 0.5 to 7.5% by weight of the compound of claim 1.

19. An emulsion explosive comprising an emulsion of an aqueous solution of an oxidiser salt in a liquid fuel including from 0.5 to 5% by weight based on the overall emulsion of the compound of claim 1 as an emulsifier.

20. A personal care emulsion or dispersion comprising a continuous phase of an emollient oil having dispersed therein a water based liquid, or a hydrophile phase and including the compound of claim 1 as an emulsifier and/or dispersant.

21. The dispersion as claimed in claim 20 which includes one or more sunscreen components.

22. A metal working fluid including the compound of claim 1 as an emulsifier and/or lubricant.

* * * * *